(12) United States Patent
Friberg

(10) Patent No.: US 10,894,099 B2
(45) Date of Patent: Jan. 19, 2021

(54) MULTI FUNCTIONAL SHOE SANITIZER AND METHOD OF USING IT

(71) Applicant: Walter Friberg, Highland Park, IL (US)

(72) Inventor: Walter Friberg, Highland Park, IL (US)

(73) Assignee: Walter S. Friberg, Highland Park, IL (US)

( * ) Notice: Subject to any disclaimer, the term of this patent is extended or adjusted under 35 U.S.C. 154(b) by 486 days.

(21) Appl. No.: 15/706,762

(22) Filed: Sep. 18, 2017

(65) Prior Publication Data
US 2019/0083666 A1   Mar. 21, 2019

(51) Int. Cl.
| | |
|---|---|
| *A61L 2/00* | (2006.01) |
| *A61L 2/08* | (2006.01) |
| *A61L 2/10* | (2006.01) |
| *A61K 36/61* | (2006.01) |
| *A61K 36/53* | (2006.01) |

(Continued)

(52) U.S. Cl.
CPC ............ *A61L 2/0047* (2013.01); *A61K 36/14* (2013.01); *A61K 36/185* (2013.01); *A61K 36/53* (2013.01); *A61K 36/61* (2013.01); *A61K 47/46* (2013.01); *A61L 2/0052* (2013.01); *A61L 2/0058* (2013.01); *A61L 2/084* (2013.01); *A61L 2/085* (2013.01); *A61L 2/10* (2013.01); *A61L 2/26* (2013.01); *A61L 9/20* (2013.01); *C02F 1/30* (2013.01); *C02F 1/32* (2013.01); *C02F 1/325* (2013.01); *A61L 2202/11* (2013.01); *A61L 2202/21* (2013.01); *A61L 2202/26* (2013.01);

(Continued)

(58) Field of Classification Search
CPC ... A61L 2/08; A61L 2/10; A61L 2/084; A61L 2/085; A61L 2/0052; A61L 2/0047; A61L 2/0058; C02F 1/30; C02F 1/32; C02F 1/325

See application file for complete search history.

(56) References Cited

U.S. PATENT DOCUMENTS

| | | |
|---|---|---|
| 5,978,996 A | 11/1999 | Ullman |
| D620,095 S | 7/2010 | Ullman et al. |

(Continued)

OTHER PUBLICATIONS https://www.ciriscience.org/a_96-Study-Reveals-High-Bacteria-Levels-on-Footwear Created on May 3, 2008. by Dr. Charles Gerba, microbiologist Last Modified on May 3, 2008.

*Primary Examiner* — Sean E Conley

(57) ABSTRACT

Portable multifunctional device designed for sanitizing of inner and outer surfaces of shoes, sanitizing of air, water, household items and surfaces, treatment of skin and wound infection, nails fungus, cosmetic use, and detection of counterfeit currency. The device is able to perform all the above sanitizing, therapeutic and cosmetic functions that would otherwise be carried out by various different devices. The enhance functionality has been accomplished without alteration of any parts of the device. Apparatus utilizes light radiation in three diapasons: 100-280, 405-495, and 700-1064 nm and provides distant sanitizing. Apparatus comprises at least one module with a dual DC-AC power supply. Each module has a germicidal unit, retractable flexible shaft, shade, and housing. The flexible shaft allows positioning the germicidal units under different angle for uniform distant illumination. The device is suitable for household, traveling, and military use.

2 Claims, 2 Drawing Sheets

(51) Int. Cl.
  *A61K 36/185* (2006.01)
  *A61K 36/14* (2006.01)
  *A61K 47/46* (2006.01)
  *C02F 1/30* (2006.01)
  *A61L 2/26* (2006.01)
  *C02F 1/32* (2006.01)
  *A61L 9/20* (2006.01)
  *G01N 21/64* (2006.01)

(52) U.S. Cl.
  CPC ...... *C02F 2303/04* (2013.01); *G01N 21/6447* (2013.01)

(56) References Cited

U.S. PATENT DOCUMENTS

| | | |
|---|---|---|
| 8,466,433 B2 | 6/2013 | Ullman |
| D693,450 S | 11/2013 | Barlam |
| 8,895,938 B2 | 11/2014 | Ullman |
| D738,478 S | 9/2015 | Ullman et al. |
| 9,162,000 B2 | 10/2015 | Ullman |
| 9,211,352 B2 | 12/2015 | Kassel et al. |
| 9,308,393 B1 * | 4/2016 | Olvera ................ A61N 5/0616 |
| 2006/0284109 A1 * | 12/2006 | Scheir ...................... A61L 9/20 |
| | | 250/455.11 |
| 2007/0164232 A1 | 7/2007 | Tocups |
| 2011/0030241 A1 | 2/2011 | Reuben |
| 2011/0054574 A1 * | 3/2011 | Felix ................... A61L 2/0047 |
| | | 607/92 |
| 2015/0008336 A1 | 1/2015 | Rubinchikov |

* cited by examiner

MULTI FUNCTIONAL SHOE SANITIZER AND METHOD OF USING IT

FIELD OF THE INVENTION

The present invention relates to improving methods and devices for shoe sanitizing. More specifically, the invention relates to home-use ultraviolet emitting devices design to eliminate or significantly reduce harmful microorganisms inside shoes. The present invention has supplementary applications to address most of the shoe-related environmental home hazards including sanitizing interior and exterior parts of human footwear and animal paw boots, socks and gloves, air in shoe storages, sanitizing shoe mats and spaces under shoe storage furniture; the present invention has additional applications such as sanitizing small household items, water, household surfaces (carpet, linens, mattresses, pillows), therapy of nail, skin and wound infections, treatment of skin imperfections, and detection of counterfeit currency.

BACKGROUND OF THE INVENTION

Harmful microorganisms—bacteria, viruses, fungi that flourish on shoes became a serious environmental problem. These pathogenic microbes may cause multiple health issues including but not limited to hives, asthma, diarrhea, pneumonia, and nail fungus. Shoes and pet paw bouts can contaminate floor and other household surfaces. Harmful microorganisms reside on shoes has significant impact on the home entrance environment: hallway floor, mats, shoe storage furniture. Dr. Gerba from the University of Arizona found an average 2,887 units of bacteria on an inner part of the shoe and more than 421,000 units of bacteria on outer part of shoe. As per Dr. Gerba, "the common occurrence (96 percent) of coliform and E. coli bacteria on the outside of the shoes indicates frequent contact with fecal material, which most likely originates from floors in public restrooms or contact with animal fecal material outdoors . . . . Our study also indicated that bacteria can be tracked by shoes over a long distance into your home or personal spaces after the shoes were contaminated with bacteria." (https://www.ciri-science.org/a_96-Study-Reveals-High-Bacteria-Levels-on-Footwear). In addition, some microbes also cause unpleasant odor. Shoe smell is a common nuance of many dwellings.

Germicidal light irradiation particularly a short wave ultraviolet (UV-C) within a range from 100 to 280 nm, especially a 254 to 260 nm diapason plays a significant role among modern methods of reducing dwelling germs. The UV-C disinfection is widely acceptable. However, the UV-C presents a hazard to eyes and skin. In addition, according to the National Toxicology Program, "Ultraviolet C radiation is reasonably anticipated to be a human carcinogen". Footwear materials are also sensitive to the ultraviolet light. UV light wavelengths shorter than 240 nm will create ozone. Ozone can cause multiple health problems in susceptible individuals especially people with lung problems, children, and older adult. The effectiveness of the UV-C disinfection is directly proportional to the dosage of radiation: dose=duration×energy/surface. High intensity with a short duration is not suitable for the home use. All home sanitizers disregard of sanitizing objects utilize a low intensity UV-C radiation over a relatively long period of time. The long period of sanitizing is one of major obstacles of acceptance of UV-C devices.

Violet-blue (VB) lights do not cause the eyes and skin damage. Violet-blue lights with waveforms within a range from 405 to 495 nm have antibacterial and antifungal properties and use for air disinfection in the hospital, treatment of skin infections, as well as in cosmetology to improve skin texture. Moreover, a part of VB spectrum blue-turquoise lights (BT) with waveforms within a range from 465 to 495 nm, especially a 465-470 nm diapason has healthy affects on vision and the sleep/wake cycle.

Borderline Far-Red lights and Near Infrared rays (FR/NIR) at physiological temperature (non-thermal) with waveforms within a range from 700 to 1064 nm, especially a 700-930 nm diapason exhibits antibacterial and fungal effects. The FR/NIR illumination utilizes in cosmetology to skin rejuvenation.

The non-laser, non-thermal FR/NIR and non-laser BT have germicidal properties and don't have harmful effects on human eyes and skin.

Another obstacle of acceptance of the UV-C home sanitizing devices is their narrow scope of use. All home sanitizers including shoe antimicrobial devices are highly specialized. For example, one device can be used only for air sanitizing, and another one—only for inner shoe surfaces sanitizing. It creates a significant financial border and makes almost impossible to use all devices during travelling or on a military field.

The purposes of the proposal invention are increase effectiveness of sanitizing process with simultaneous decrease potentially harmful ultraviolet exposure, decrease time of procedure; improve user's safety, and increase functionality and portability of shoe sanitizing devices.

DESCRIPTION OF THE RELATED ART

There are multiple apparatus utilizing antimicrobial effects of the ultraviolet radiation for sanitizing of interior portions of human footwear: U.S. Pat. Nos. 9,162,000; 9,211,352; 8,895,938, US D6 20095; US 20150008336; U.S. Pat. No. 5,978,996, US 20070164232, US 20110030241.

All of the above devices utilize a low intensity and long duration of sanitizing. They also use similar sources and parameters of UV-C radiation.

The previous art UV-C inner shoe surface sanitizers comprise three essential parts: a UV-C light unit located at an anterior (forepart) of shoe, a power supply located at a posterior (heel) part and an ultraviolet protection container. The UV-C light unit further comprises a UV-C light source inserted inside of a light guard and an electrical (non-light-emitting) unit (US 20150008336; U.S. Pat. Nos. 8,466,433; 5,978,996; US D693450; US D738478 S1).

During the sanitizing procedure the previous art device placed on an inner shoe surface, and then each shoe is put into a protective container to prevent a user from ultraviolet exposure (U.S. Pat. No. 8,895,938). Pathogenic microbes can accumulate on an inner surface of the container due to direct contact shoe soles. The above mentioned Dr. Gerba's research showed that much more bacteria reside on shoe soles than on inner shoe parts. The container itself becomes a source of infection, In previous art sanitizers whole devices are put on inner shoe surfaces as close as possible to their foreparts. The previous art sanitizers don't provide uniform illumination of all treated surfaces. Only the anterior shoe part undergoes direct exposure of the germicidal radiation and the rest parts of the shoe are left untreated. The non-light emitting electrical unit blocks germicidal rays and prevents the rest of the inner shoe from the light exposure. In addition, due to the direct contact the device with the inner shoe surface, the area under the device also can't be treated.

The previous art shoe sanitizer process is unsafe because it creates a significant possibility to transfer harmful microbes from one shoe to another during subsequent sanitizing due to the direct contact of an inner shoe (insole) with the device's components (light guard and electrical unit) and the most contaminated outer part of shoe (sole) with an inner container surface. The previous art light guards have a closed design due to possibility of light sources damage during the direct contact with treating surfaces. The closed design of the light guards blocks a significant amount of germicidal rays.

The previous art inner shoe surface sanitizers cannot be used for sanitizing of outer shoe surfaces, floor and other household surfaces contaminated by shoes, and air in shoe storages due to fundamental design issues.

SUMMARY OF THE INVENTION

The present invention addresses the above-mentioned shortcomings and achieves the following goals:

1. Increase effectiveness and decrease time of germicidal process with simultaneous decrease dose of potentially harmful ultraviolet radiation.
2. Address most of footwear-related home microbial hazard problems.
3. Perform the inner shoe surface sanitizing without placing treating shoes inside of the protective container.
4. Improve user's safety.
5. Increase portability to make the proposal device suitable for travelling and military (field) use.

The proposal "all in one" device designs to address most of footwear-related microbial hazard problems. It eliminates the necessity to buy multiple devices that narrow specialized for only one type of shoe sanitizing. The proposal apparatus is suitable to address multiple footwear-related home microbial hazard problems including but not limited to sanitizing of inner and outer shoe surfaces, socks, household surface contaminated by shoes and air in shoe storages; sanitizing a hallway floor, carpet mats, shoe storage furniture. The present invention has additional applications for sanitizing household items, water, treatment of nail, skin, and wound infections, cosmetic use and detection of counterfeit currency.

The proposal device is able to perform all the above sanitizing, therapeutic and cosmetic functions that would otherwise be carried out by various different devices.

The enhance functionality has been accomplished without alteration of any parts of the proposal device or adding additional parts.

The preferable embodiment (FIG. 1) comprising at least one module wherein each of the modules comprising a germicidal unit 1 a retractable flexible shaft 2, a detachable shade 3, and a housing 4, said module has an internal and/or external power supply 5 (FIGS. 1 and 2), said retractable flexible shaft 2 connects said germicidal unit 1 with said housing 4, said germicidal unit 1 comprising at least two detachable germicidal light sources 6 and a detachable guard 7 (FIGS. 1 and 2), said detachable shade 3 slides along said flexible shaft 2 and secures in place in an appropriate position depends on object of sanitizing.

Said flexible shaft 2 provides a position of said germicidal unit under any appropriate angle to deliver uniform illumination of treating surfaces without direct contact any part of said device with them. The distant sanitizing increases effectiveness of the process because parts of the proposal device don't block germicidal rays and can't be contaminated. It also prevents transferring harmful microbes from on treating object to another.

Said guard 7 (FIGS. 1 and 2) protects said light sources from mechanical damage and at the same time doesn't block germicidal rays. The proposal invention utilizes two types of said detachable guard: an interchangeable protective case (FIG. 1) and an open protector (FIG. 2). Depending on purposes either one of said guard 7 or only said interchangeable protective case can be employed.

Said interchangeable protective case comprising walls that completely cover said light sources from all sides. Said walls made from transparent for germicidal light materials for example an UV-C transparent material (quartz or "soft glass"). Said materials must be resistant to mechanical damage. Said light sources are placed inside of said case and hermetically sealed.

Said open protector comprising separated components with space between them; said open protector surrounds said light source.

The position of said detachable shade 3 on said flexible shaft 2 has been selected to protect a user from said germicidal radiation. During sanitizing process said detachable shade 3 secures on said flexible shaft 2. It prevents said detachable shade 3 from direct contact with treating object. For non-ultraviolet, non-laser light sources no said shades are necessary.

For the light augmentation said open protector 7 and an inner surface of said shade 3 are covered by a reflective dye.

Each module has a dual DC and AC power supply 5. The battery located inside of the housing 4. It allows using each module independently.

As an external power supply 5 can be used either a household extension cord with at least two outlets and a timer (FIG. 1) or a special holder (FIG. 2). To sanitize multiple objects simultaneously two or more modules plug either into either said household extension cord, or said special holder, or wall outlets. If said module or modules plugged in the wall outlets a user could monitor time of the procedure with a wrist watch, Said germicidal radiation selected from the group of electromagnetic waves in the ultraviolet, visible light, infrared diapasons, The proposal apparatus utilizes either only in one of the above diapasons, for example, only infrared radiation, or any combinations thereof, such as the ultraviolet and visible lights simultaneously, ultraviolet and infrared lights simultaneously, and etc. If a single diapason is selected one or more germicidal light sources can be employed. The time and intensity of each type of the germicidal radiation regulates independently.

To decrease time of shoe sanitizing, decrease dose of potentially harmful ultraviolet radiation, and increase effectiveness the proposal device employs different parts of electromagnetic spectrum simultaneously: UV-C (100-280 nm), VB (405-495 nm), and FR/NIR (700-1064 nm). UV-C, VB, and FR/NIR radiation have different mechanisms of antimicrobial action and provide synergetic germicidal effect.

The proposed apparatus utilizes different kinds of light sources 6 including but not limited to bulbs, LED's, OLED's, or lasers along or in any combinations to maximize germicidal effect.

Preferred embodiment utilizes ozone-free, low intensity, non-laser UV-C radiation within a range from 254 to 260 nm simultaneously with the low intensity, non-laser BT radiation within a range from 465 to 470 nm and/or the low intensity, non-laser FR/NIR radiation at physiological temperature within a range from 700 to 930 nm. The combination UV-C with BT and/or FR/NIR allows to lower dose of potentially harmful ultraviolet radiation with simultaneous increase the sanitizing effect.

For shoe sanitizing with simultaneous air purification instead UV-C the proposal device utilizes harmless for user's skin and eyes non-laser, blue-turquoise lights along or in conjunction with non-laser FR/NIR radiation at physiologic temperature. The blue-turquoise lights within a range from 465 nm to 470 nm besides antibacterial and antifungal properties also benefit vision and the sleep/wake cycle. Non-laser BT and non-laser, non-thermal FR/NIR rays don't require using means to protect user's eyes including said detachable shade 3 or protective glasses. If only one part of said electromagnetic spectrum utilizes, for example BT either one or more detachable germicidal light sources 6 can be used.

Proposal methods of using said proposal device described in details in the section "Methods of using the proposal device".

DETAILED DESCRIPTION OF THE INVENTION

Figure 1:
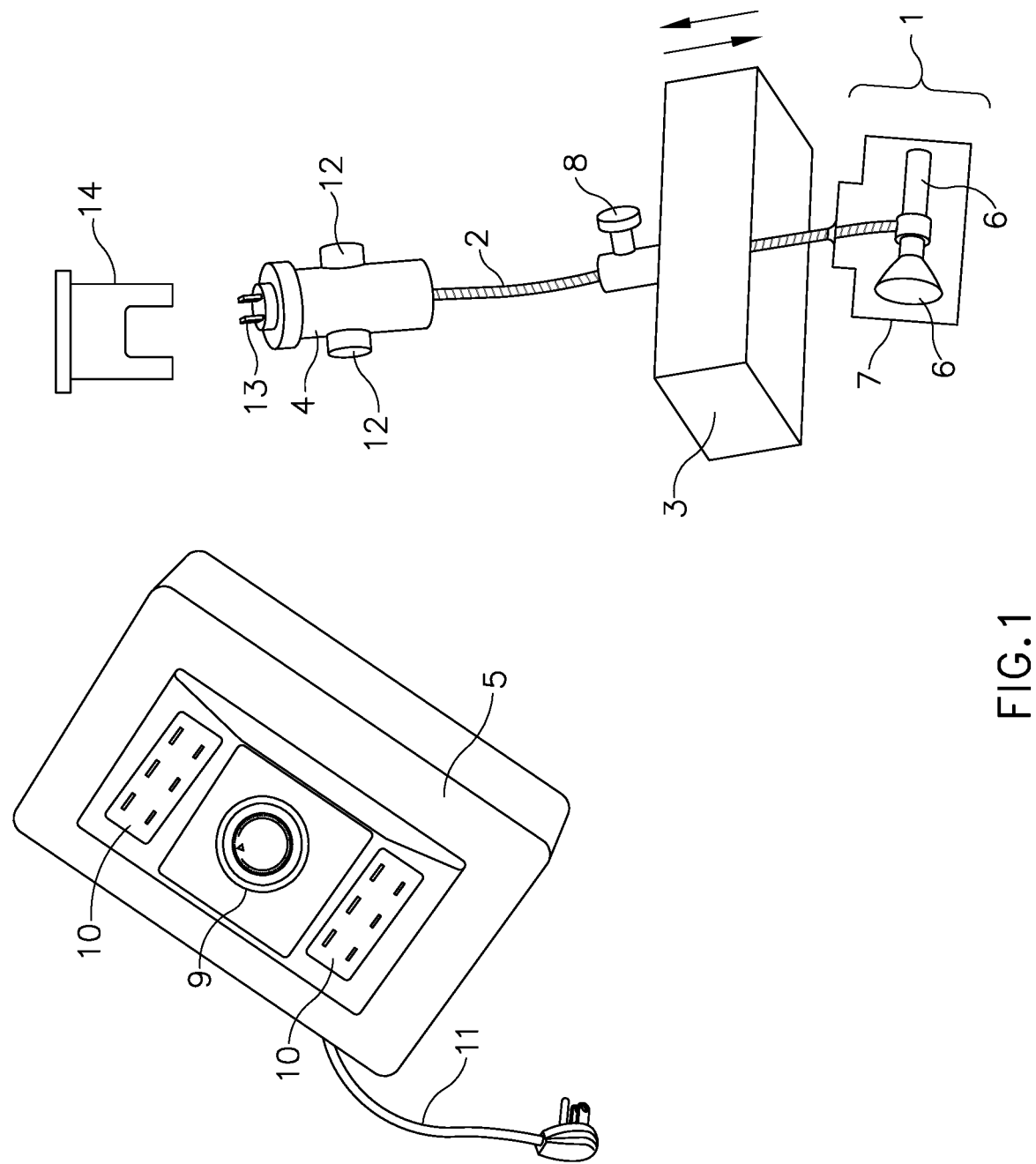
FIG. 1 represents parts of the proposal apparatus with a household extension cord as an external power supply FIG. 2 demonstrates a position of the proposal device inside of shoe

While the present invention is susceptible to various modifications and alternative forms, specific aspect thereof has been shown by way of example and drawings and will be described in detail below. It should be understood, however, that it is not intended to limit the invention to the particular forms disclosed, but on the contrary, the invention is to cover all modifications, equivalents, and alternative falling within the spirit and the scope of the invention as defined by the appended claims.

Preferred embodiment (FIG. 1) comprising at least one module wherein each of said modules comprising a germicidal unit 1, a retractable flexible shaft 2, a detachable shade 3, and a housing 4, said germicidal unit 1 connects to said housing 4 via said flexible retractable shaft 2, said germicidal unit 1 comprising at least two detachable germicidal light sources 6 and a detachable guard 7 (FIGS. 1 and 2), said shade 3 slides along said shaft 2 and secures in place in an appropriate position by a stopper 8, said modules has a dual power supply: internal (DC), for example, a rechargeable battery and external (AC), said internal power supply 5 is located inside of said housing 4, said external power supply 5 (FIGS. 1 and 2) has a timer 9, at least two outlets 10, and a retractable cord 11. The proposal invention utilizes either one of two types of said external power supply 5: the household extension cord (FIG. 1) and the expendable holder (FIG. 2), or wall outlets.

Each of said modules can be used either along or simultaneously with other modules.

Said light sources 6 and said guard 7 are detachable. Said guard 7 protects said light sources from a mechanical damage and doesn't block germicidal lights. The proposal invention utilizes one of two types of said guard 7: said interchangeable protective case (FIG. 1) and said open protector (FIG. 2).

Said interchangeable protective case is hermetically sealed said light sources. (FIG. 1). Said protective case comprising walls that completely cover said light sources from all sides. Said walls made from transparent for germicidal light materials that are resistant to mechanical damage Said light sources are placed inside of said case. Said case can be easily replaced and cleaned between sanitizing. It improves hygiene, decrease risk of transferring infection. Having several said interchangeable protective cases a customer can use the same module for different sanitizing, therapeutic, and cosmetic purposes. Additionally, using said case allows performing light irradiation simultaneously with mechanical skin stimulation—massaging during cosmetic procedures. For example, after shoe sanitizing a user is able to perform a cosmetic light self-massage using the same module after replacing said interchangeable protective case. The combination of said light exposure with massage increases effect of the light therapy by increasing blood circulation, decreasing pain and muscle tension. Lastly, said case makes possible using the proposal device for an additional tap water sanitizing by immersing a dedicated interchangeable protective case in glass of water.

Figure 2:
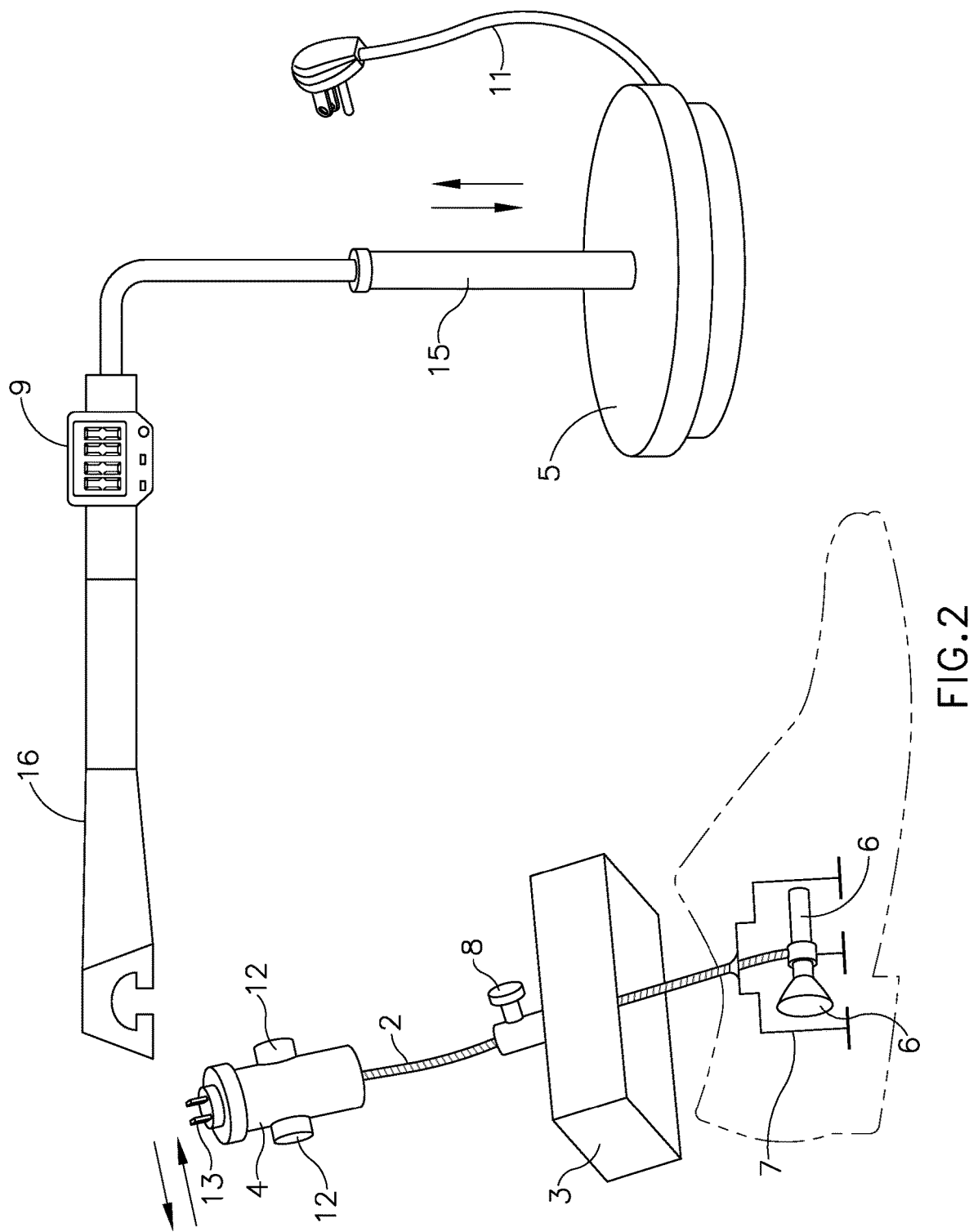

Said open protector comprises separated elements with space between them and surrounds said light sources (FIG. 2). In certain embodiment said open protector comprises a horizontal base and at least three vertical pins wherein said pins inserted in said base, wherein the height of said pins exceed the height of said light source.

Said shade 3 slides along said shaft 2 and secures in an appropriate position depending on a treating object. For non-ultraviolet, non-laser light sources no said shades are necessary. To increase light augmentation the inner surface of said shade 3 and said open protector are covered by a reflective dye.

Said housing 4 (FIGS. 1 and 2) is used as a holder and as a dual AC-DC power supply for its module. Said housing 4 has at least two switches 12 and a plug 13. Said switches 12 regulate intensity of the germicidal radiation. Said plug 13 connects with either said external power supply 5 or a wall socket. Said holder 4 is able to accommodate said retractable flexible shaft 2. Said plug 13 is protected from a mechanical damage by a cover 14. Said cover 14 may serve as a pedestal for its module if said rechargeable battery is in use.

Said external power supply 5 also serves as a support for one or more modules. Said external power supply 5 can be used said household extension cord (FIG. 1) or said expendable holder (FIG. 2). Said holder (FIG. 2) has a vertical adjustable stand 15 and a horizontal power strip 16 with said outlets 10 inside. Wall outlets also can be used as a support of said modules.

Position of said germicidal unit 1 with respect of said housing 4 depends on types of said power supply 5: said housing 4 can either sit on said extension cords in an upward position or hang on said holder in a downward position (FIG. 2). Using said holder is more convenient for home use because it allows easily accommodating different types of shoes including the knee-high and over-the-knee-high shoes. Using of said internal power supply and utilizing the wall outlets as a device support and for charging batteries increases portability and makes proposal device suitable for travelling.

Methods of Using of the Proposal Device

The below examples of proposal methods of using of the proposal device are mentioned to show only those specific details that are pertinent to understanding the aspects of the present invention so as not to obscure the disclosure with details that will be readily apparent to those of ordinary skill in the art having benefit of the description herein. The most of the proposal methods utilize the proposal apparatus comprising at least one module wherein each module comprising a germicidal unit, a detachable shade, a retractable flexible shaft, and a housing, said retractable flexible shaft connects said germicidal unit with said housing, said detachable shade slides along said flexible shaft and secures in place in an appropriate position depends on object of sanitizing, said germicidal unit comprising a detachable guard and at least two detachable germicidal light sources; said flexible shaft provides positions of said germicidal unit under any appropriate angle to deliver a uniform illumination of treating surfaces without direct contact any part of said apparatus with said surfaces; said detachable guard comprising interchangeable protective case, said interchangeable protective case comprising walls that completely cover said light sources from all sides, said walls made from materials that is transparent for said germicidal light and resistant to mechanical damage, said light sources are placed inside of said case and hermetically sealed. Proposal methods utilize detachable germicidal light sources, wherein each germicidal light source emits radiation in one of the following germicidal diapasons: UV-C within a range from 100 to 280 nm, VB within a range from 405 to 495 or FR/NIR within a range from 700 to 1064 nm. Proposal methods utilize either one or more of said germicidal light sources if only one of said diapasons is selected or at least two of said germicidal light sources if more than one of said diapasons are selected.

To decrease a dose of the potentially harmful ultraviolet radiation, said ultraviolet rays are used simultaneously with said violet-blue rays and/or with said far-red/near-infrared rays.

The most of the proposal methods utilizes the following the most effective germicidal wavelengths: a part of UV-C diapason from 254 to 260 nm, a part of the Violet-Blue diapason—the Blue-Turquoise diapason from 465 to 470 nm and the Far-Red and Near Infrared diapason from 700 to 930 nm.

Each germicidal diapason can be used either as a single source of germicidal radiation or simultaneously with others in any combinations: UV-C+VB, UV-C+FR/NIR, VB+FR/NIR, UV-C+VB+FR/NIR depending on the specific sanitizing, therapeutic, or cosmetic purposes.

The proposal device utilizes laser and non-laser sources of radiation in any combinations. If laser sources of radiation are utilized users must wear protective glasses. The preferred embodiment utilizes the low intensity, ozone-free, non-laser UV-C germicidal radiation simultaneously with the non-laser, low intensity VB and/or non-laser, non-thermal, low intensity FR/NIR radiation. Said combinations increase germicidal effect, decrease dose of ultraviolet radiation, and improve user's safety.

Certain embodiments utilize non-laser VB along or simultaneously with non-laser, non-thermal FR/NIR radiation. Non-ultraviolet, non-laser sources of radiation don't require using means to protect user's eyes, for example, said shades 3 and/or protective glasses. If only one part of said electromagnetic spectrum utilizes, such as BT either one or more detachable germicidal light sources 6 can be used.

Sanitizing time can be set by the timer 9 or recorded with a hand watch. If external power supply is used the modules can be plugged into either said external power supply units 5, or wall sockets. Alternatively, said internal power supply of modules can be used; in such case modules should be placed in upright position on a flat surface on covers 14. Positions of the shades 3 on the flexible shafts 2 are secured by the stoppers 8. To start sanitizing said switches 12 should be turned in "on" position. Switches 12 also regulate intensity of the germicidal radiation.

The dose of radiation produced by the proposal device is directly proportional to the power of the said germicidal light sources and time of exposure. The dose of radiation should be sufficient to significantly reduce a number of harmful microorganisms by making them substantially incapable of reproducing with or without killing them. In the United States for devices that were patented and/or produced under names "shoe sterilizer" or "shoe sanitizer", the dose of radiation has been not defined according to the appropriate standards. However, the United States Environmental Protection Agency (EPA) defines a sanitizer as an antimicrobial agent "that reduces but does not necessarily eliminate all the microorganisms on a treated surface." To be classified as a sanitizer, a product needs to demonstrate a three log (or 99.9%) reduction of targeted microbes. On the other hand, a sterilizer must achieve at least a six log reduction, or 99.9999% of selected microorganisms.

The time of procedure will be determined by the specific sanitizing, therapeutic, or cosmetic goals. The period of the germicidal light exposure ranges from several seconds to tenth minutes. The amount of energy is measured in mJ/cm2. The proposed device allows regulating the amount of different spectrum of electromagnetic radiation separately. To compare with the previous art devices employing UV-C along the proposed methods utilize the significantly lower amount of the potentially harmful UV-C energy. Proposed methods of sanitizing exercise synergetic germicidal effect of the simultaneous application UV-C with other germicidal parts of electromagnetic spectrum, for example, VB and/or FR/NIR.

Method 1: sanitizing of inner surfaces of footwear by using the proposal device (FIG. 2). Proposal method can be used for all types of shoes including casual shoes, sport shoes, military and over-the-knee high boots. For sanitization of inner surfaces of most of the types of shoes, the shoes placed in upright position and the knee-high and over-the-knee high boots placed in a horizontal position—on side. To sanitize two pairs of shoes four modules are used simultaneously.

Said method comprising selecting a non-laser germicidal unit having at least one of said light sources emitting ultraviolet radiation with waveforms from 254 to 260 nm and at least one of said light sources emitting blue-turquoise radiation with waveforms from 465 to 470 nm, said ultraviolet and blue-turquoise rays illuminating treating surfaces simultaneously, inserting said germicidal units into shoes without direct contact with inner shoe surfaces, placing said shades in close proximity to the upper part of the shoes without direct contact with said upper part of the shoes, securing said shades on said flexible shaft in the appropriate position, selecting intensity and duration of germicidal radiation necessary for sanitizing.

Method 2: sanitizing of inner surfaces of footwear with simultaneous air sanitizing in shoe storage by using the proposal device. Said method is suitable for small, poorly ventilated areas and as a supplemental air improvement in a shoe closet simultaneously with sanitizing of inner surfaces of footwear. For sanitization of inner surfaces of most of the types of shoes, the shoes placed in upright position and the knee-high and over-the-knee high boots placed in a horizontal position—on side.

Said method comprising selecting a non-laser germicidal unit having at least one source emitting blue-turquoise radiation within a range from 465 to 470 nm, removing said shades, inserting said germicidal units into shoes without direct contact with inner shoe surfaces, selecting intensity and duration of germicidal radiation necessary for sanitizing.

Another embodiment comprising selecting a non-laser germicidal unit having at least one of said light sources emitting blue-turquoise radiation within a range from 465 to 470 nm and at least one of said light sources emitting non-thermal FR/NIR radiation within a range from 700 to 930 nm, said blue-turquoise and FR/NIR rays illuminating treating surfaces simultaneously, removing said shades, inserting said germicidal units into shoes without direct contact with inner shoe surfaces, selecting intensity and duration of germicidal radiation necessary for sanitizing.

Method 3: Air Sanitizing Around o'Clock

A method comprising selecting a non-laser germicidal unit having one or more lighting sources emitting blue-turquoise light radiation with waveforms from 465 to 470 nm and placing said flexible shaft in upright position.

Method 4: sanitizing of outer surfaces of footwear by using the proposal device. Said method comprising mechanically removing soiling, placing shoes on side, directing said germicidal units to soles, selecting two or four modules depending on the shoe sizes, selecting a non-laser germicidal unit having at least one of said light sources emitting ultraviolet radiation with waveforms from 254 to 260 nm and at least one of said light sources emitting blue-turquoise radiation with waveforms from 465 to 470 nm, said ultraviolet and blue-turquoise rays illuminating treating surfaces simultaneously, advancing said germicidal units to the treating surfaces without direct contact with them, covering said germicidal units by said shades without direct contact with the treating surfaces, selecting intensity and duration of germicidal radiation necessary for sanitizing.

Method 5: sanitizing of soft-shoes including animal soft shoes and toddlers soft sole shoes, socks, and gloves by using proposal device.

For persons suffering from skin and nail infections and pet items ether dedicated modules or dedicated case guards must be used. After sanitizing an inner surface, repeating the sanitizing process turning said soft-shoes and gloves inside out; sanitizing sock should be performed after laundering.

Said method comprising selecting a non-laser germicidal unit having at least one of said light sources emitting ultraviolet radiation with waveforms from 254 to 260 nm and at least one of said light sources emitting blue-turquoise radiation with waveforms from 465 to 470 nm, said ultraviolet and blue-turquoise rays illuminating treating items simultaneously, placing treating items on a flat surface preferable on a piece of foil to increase reflection, advancing said germicidal units to the treating items without direct contact with them, covering said treating items by said shade without direct contact inner surfaces of said shade with said treating items, selecting intensity and duration of germicidal radiation necessary for sanitizing.

Method 6: Sanitizing of Hard-to-Reach Areas by Using the Proposal Device.

Said method can be used for any hard-to-reach areas for example under furniture. Said method comprising selecting a non-laser germicidal unit having at least one of said light sources emitting ultraviolet radiation with waveforms from 254 to 260 nm and at least one of said light sources emitting blue-turquoise radiation with waveforms from 465 to 470 nm, said ultraviolet and blue-turquoise rays illuminating treating areas simultaneously, placing one or more modules on a floor under furniture, advancing said germicidal units toward said treating areas, advancing said shades toward the furniture without direct contact with it, setup appropriate intensity of germicidal radiations and leaving said module or modules in place for the time necessary for sanitizing.

Method 7: Sanitizing of Household Surfaces by Using the Proposal Device

Said method can be used for sanitizing shoe mats, stoves, sinks, certain toys, countertops, flatware, plates, and tools.

Said method comprising selecting a non-laser germicidal unit having at least one of said light sources emitting ultraviolet radiation with waveforms from 254 to 260 nm and at least one of said light sources emitting blue-turquoise radiation with waveforms from 465 to 470 nm, said ultraviolet and blue-turquoise rays illuminating said treating surfaces simultaneously, directing said module perpendicularly to said treating surface, advancing said germicidal units toward said treating surface, covering said germicidal units by said shades without direct contact with said treating surface, slowly moving said module along said treating surfaces without direct contact with them.

Method 8: prevention and treatment of nail fungus infection by using the proposal device.

Said method designs to target pathogenic microbes not only on nails but also on footwear and gloves. For better hygiene and increase effectiveness, patients with nail fungus infection should use personal modules or personal cases and sanitize inner shoe surfaces and insoles separately. Said method comprising sanitizing of inner surfaces of footwear if at least one toenail is infected, sanitizing of inner surfaces of socks if at least one toenail is infected according to the method 1, sanitizing of inner surfaces of gloves if at least one fingernail is infected according to the method 5, applying a proper composition of essential oils having antifungal, antimicrobial, and deodorizing properties to all fingernails of both upper limbs if at least one fingernail is infected, or to all toenails of both lower limbs if at least one toenail is infected, said composition comprising seven essential oils, namely: Tea Tree Oil along or mixed with Manuka Oil (Lema Oil), Thyme Oil, Lavender Oil, Geranium Oil, Rosemary Oil, Cypress Oil, *Eucalyptus* Oil, said composition comprising said essential oils with 1/7 of each by volume, said essential oils composition diluting with *Jojoba* Oil as a carrier, irradiation by germicidal rays to all fingernails of both upper limbs if at least one fingernail is infected, or to all toenails of both lower limbs if at least one toenail is infected said germicidal rays selected from the group of diapasons comprising said ultraviolet-C diapason within a range of 100 to 280 nm, said violet-blue diapason within a range of 405 to 495 nm, and said far-red/near-infrared diapason within a range of 700 to 1064 nm wherein each of said germicidal diapasons can be used for said germicidal irradiation either along or simultaneously with other diapasons in any combinations, selecting intensity and duration of germicidal radiation necessary for sanitizing.

Preferred embodiment employs non-laser UV-C within a range of 254 to 260 nm simultaneously with non-laser BT within a range of 465 to 470 nm.

Second embodiments employs non-laser UV-C within a range of 254 to 260 nm simultaneously with non-laser, non-thermal FR/NIR within a range of 700 to 930 nm.

Third embodiment employs non-laser BT within a range of 465 to 470 nm simultaneously with non-laser, non-thermal FR/NIR within a range of 700 to 930 nm.

Fourth embodiment employs non-laser UV-C within a range of 254 to 260 nm simultaneously with both non-laser BT within a range of 465 to 470 nm and non-laser, non-thermal FR/NIR within a range of 700 to 930 nm.

Fifth embodiment employs thermal 1064 nm laser NIR impulses producing by laser systems, for example Aerolase or Alma NIR handpiece.

Said proposal blend of essential oils increases antifungal activity of germicidal lights, decreases risk of re-infection, and helps to cool down nails after the laser thermal NIR procedure. Said proposal blend of essential improves appearance of affected nails and has antifungal, antimicrobial, and deodorizing properties, The application of said blend of essential oil blend should be performed daily on a regular basis and in addition after contact with water (taking a shower, swimming), and after a germicidal irradiation of nails. Patients should advise to massage nails and cuticles using disposable Q-tips with a small amount of the proposed blend.

Method 8: Therapeutic Applications and Cosmetic Applications the Proposal Device Said method can be used for wound care, treating acne, wrinkles, eczema, rosacea, and improve skin appearance. These applications are designed only for health professionals or performed by patients under proper supervision. All parts of the apparatus and particularly said shades must be carefully clean. Using said interchangeable protective cases are preferably. Selecting wavelength diapasons, intensity, and duration of radiation depends on clinical indications. During cosmetic procedure direct contact said case with skin may have additional benefits. If clinically indicated said light therapy can be combining with massage by said case with or without said essential oil blend of method 7. Said method comprising covering skin outside of the treating area, selecting germicidal light sources from the group comprising said germicidal light sources emitting ultraviolet radiation with waveforms from 254 to 260 nm, violet-blue radiation with waveforms from 405 to 490 nm, and Far-Red/Near-Infrared radiation with waveforms from 700 to 1064 nm, wherein each said germicidal diapason can be used either as a single source of germicidal radiation or simultaneously with other said diapasons in any combinations, advancing said shades to said treating areas for example, cheeks without touching them, advancing said germicidal units closer to treating areas with or without touching them, selecting intensity and duration of radiation necessary for specific indications.

The combination of said light exposure with massage increases effect of the light therapy by increasing blood circulation, decreasing pain and muscle tension. If non-laser, non-thermal BT and/or FR/NIR rays are used no shades, skin or eye protection means are necessary.

Method 9: Verification of Authenticity of Documents by Using the Proposal Device Size of the proposal module is not significantly exceeding the dimensions of modern counterfeit money detectors. A user can utilize during travelling one said module as a counterfeit money detector and sanitizer for the most important sanitizing purposes.

The proposal device may be used to detect whether a banknote (or an official item) is genuine or counterfeit. By illuminate banknotes the proposal device provides an UV and/or VB counterfeit detection and able to verify whether or not the UV marks including security threads are present on the banknote.

Said method comprising selecting germicidal light sources from the group comprising said germicidal light sources emitting ultraviolet radiation with waveforms from 254 to 260 nm, violet-blue radiation with waveforms from 405 to 495 nm, wherein each of said germicidal diapasons can be used either as a single source of radiation or simultaneously with the other, placing said module under angle between 30° to 80° with respect of a detecting object, advancing said germicidal units closer to said object without touching it to visualize the specific glowing pattern.

Method 10: Method of tap water sanitizing by using the proposal device.

Said method especially indicated when the tap water quality is questionable, for example during travelling overseas. A user should have a dedicated interchangeable protective case. Some studies show that the most effective water disinfection properties has diapason in a range of 275-280 nm. No said shades or other user's protections are necessary.

Said method comprising selecting a non-laser germicidal unit having at least one of said light sources emitting ultraviolet radiation with waveforms from 254 to 260 nm and at least one of said light sources emitting violet-blue lights with waveforms from 405 to 495 nm, said ultraviolet and violet-blue rays illuminating said tap water simultaneously, immersing said module in glass water so that water covers only said interchangeable protective case, gently shaking the glass for better sanitizing, selecting intensity and duration of germicidal radiation necessary for sanitizing.

I claim:

1. A multifunctional sanitizing apparatus comprising:
   one or more modules, wherein each module comprises:
   a housing having a plug for connection to a wall socket or external power supply;
   a germicidal unit comprising a detachable guard and at least two germicidal light sources, wherein said detachable guard is a case formed from a germicidal transparent material that hermetically seals the at least two germicidal light sources within an interior of the case, wherein a shape of said guard corresponds to a shape of an object being sanitized;
   a retractable flexible shaft having a first end and a second end, wherein the first end is directly attached to the housing and the second end is directly attached to the germicidal unit;
   a detachable shade that slides along the retractable flexible shaft and is secured in placed on the flexible shaft by a stopper which prevents said detachable shade from direct contact with the object being sanitized;
   a cover to protect said plug from mechanical damage and serve as a pedestal for the module;
   a reflective coating located in an inner surface of the detachable shade;
   an internal power supply located within said housing;
   an external power supply with a timer;
   and two switches located on said housing for regulating intensity of germicidal radiation emitted by the germicidal unit.

2. The multifunctional sanitizing apparatus of claim 1, wherein the at least two germicidal light sources emit radiation at a wavelength within a range selected from 100 to 280 nm, 405 to 495 nm, or 700 to 1064 nm.

* * * * *